United States Patent [19]
Rasmusson

[11] Patent Number: 5,458,657
[45] Date of Patent: Oct. 17, 1995

[54] ENDOSKELETAL PROSTHESIS HAVING ADJUSTABLE COUPLING

[75] Inventor: James K. Rasmusson, Birmingham, Mich.

[73] Assignee: Becker Orthopedic Appliance Company, Troy, Mich.

[21] Appl. No.: 121,038

[22] Filed: Sep. 16, 1993

Related U.S. Application Data

[63] Continuation of Ser. No. 810,623, Dec. 19, 1991, abandoned.

[51] Int. Cl.$^6$ ........................................ A61F 2/62
[52] U.S. Cl. ........................ 623/38; 403/90; 403/362
[58] Field of Search ........................ 623/27, 38, 39; 403/56, 90, 125, 362, 76, 131

[56] References Cited

U.S. PATENT DOCUMENTS

| 973,558 | 10/1910 | Pierce | 403/90 X |
|---|---|---|---|
| 3,059,948 | 10/1962 | Thompson et al. | 403/90 |
| 3,206,235 | 9/1965 | Albinson et al. | 623/38 X |
| 3,588,025 | 6/1971 | Gersman | 403/90 X |
| 3,790,965 | 2/1974 | Gelbeneggar | 403/90 X |
| 4,157,876 | 6/1979 | DiGiulio | 403/125 X |
| 4,676,800 | 6/1987 | Chen | 623/38 |
| 5,013,325 | 5/1991 | Rennerfelt | 623/38 |
| 5,047,063 | 9/1991 | Chen | 623/38 |
| 5,139,524 | 8/1992 | Aulie et al. | 623/38 |
| 5,249,766 | 10/1993 | Vogt | 403/90 X |

FOREIGN PATENT DOCUMENTS

| 1502061 | 11/1967 | France | 623/38 |
|---|---|---|---|
| 2530945 | 2/1984 | France | 623/38 |
| 2630641 | 11/1989 | France | 606/88 |
| 2605644 | 9/1976 | Germany | 623/38 |
| 3937379 | 5/1991 | Germany | 623/38 |
| 0721094 | 3/1980 | U.S.S.R. | 623/38 |
| 1026803 | 7/1983 | U.S.S.R. | 623/38 |
| 1217404 | 3/1986 | U.S.S.R. | 623/38 |
| 1391642 | 4/1988 | U.S.S.R. | 623/33 |
| 1553115 | 3/1990 | U.S.S.R. | 623/38 |
| 1161666 | 8/1969 | United Kingdom | 623/38 |

OTHER PUBLICATIONS

Pet Supply Company Catalog, Fifth Edition, 1987.

*Primary Examiner*—David H. Willse
*Attorney, Agent, or Firm*—Jenner & Block

[57] ABSTRACT

An endoskeletal system having an adjustable adapter assembly is disclosed. In one embodiment the adapter assembly utilizes a ball-and-post coupler to adjustably couple an endoskeletal pylon to a stump socket or artificial foot or hand. The adapter assembly includes a cylindrical collar which is fastened to one end of the pylon. The interior bore of the collar is spherically contoured to form a seat for receiving a bulbous end of the ball-and-post coupler, which itself is fastened to the stump socket via a socket adapter plate. The spherical interface of the ball-and-post coupler and the seat forms a articulable bearing.

27 Claims, 5 Drawing Sheets

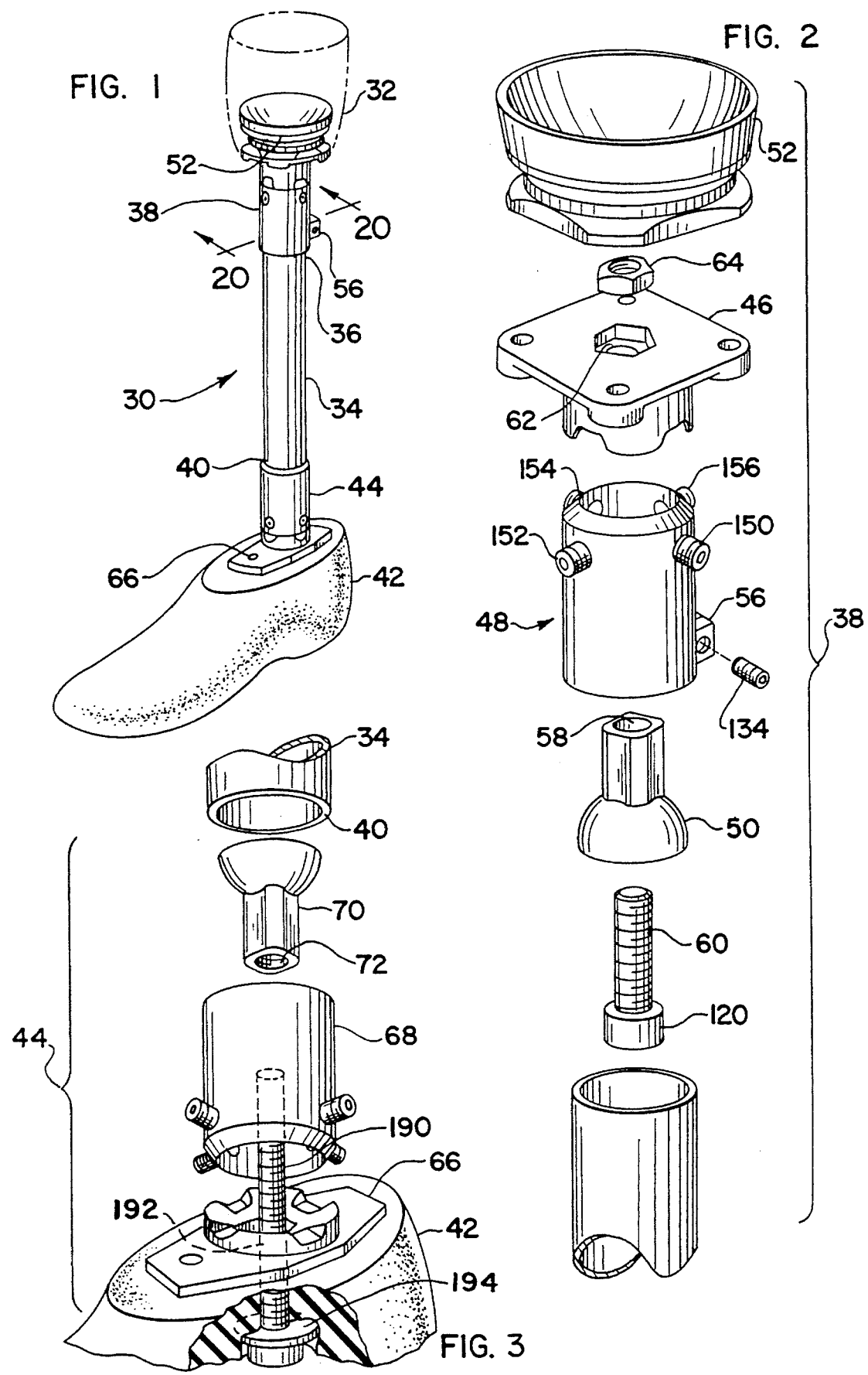

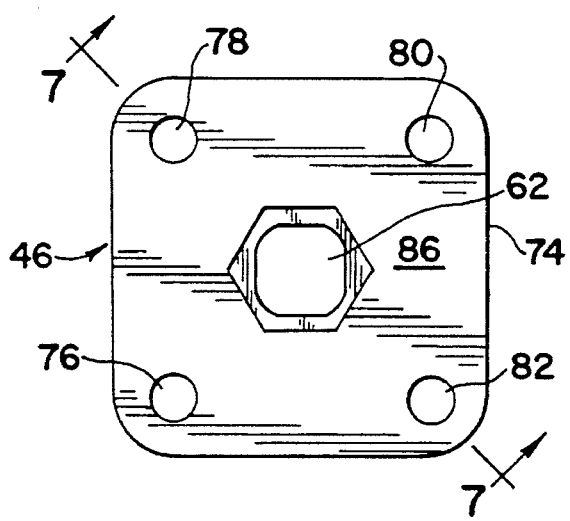
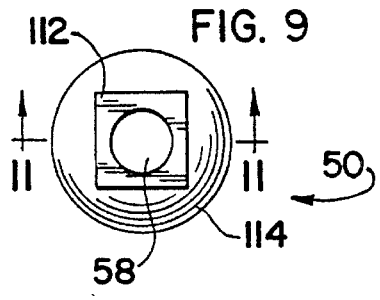
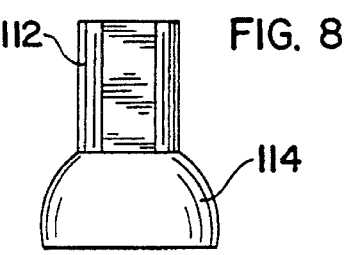
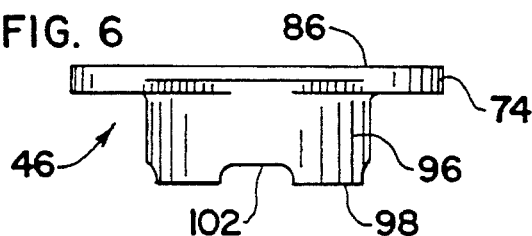
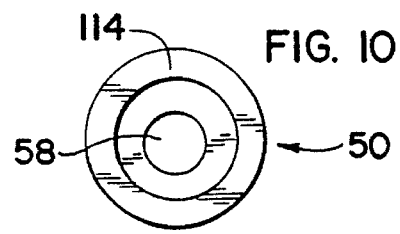
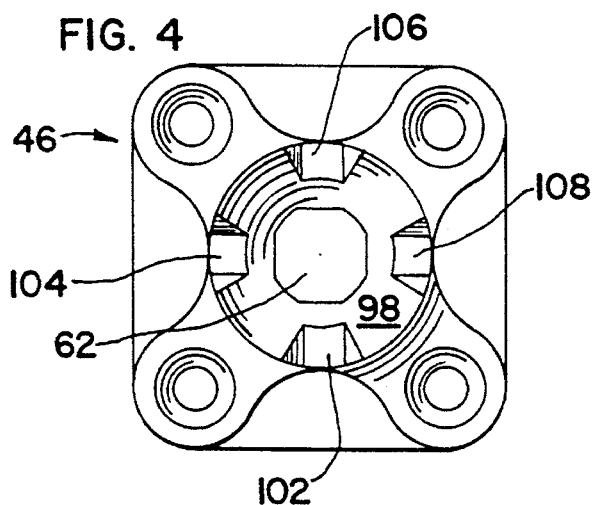
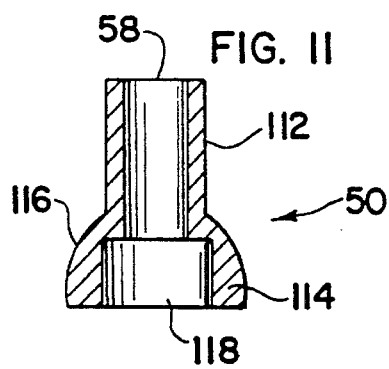
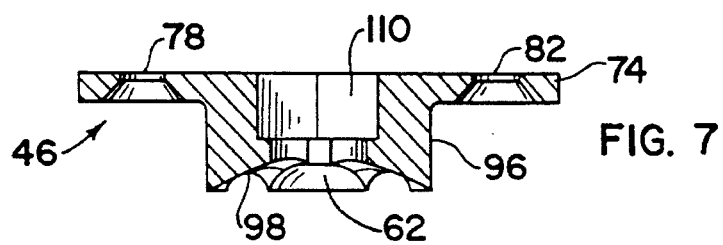

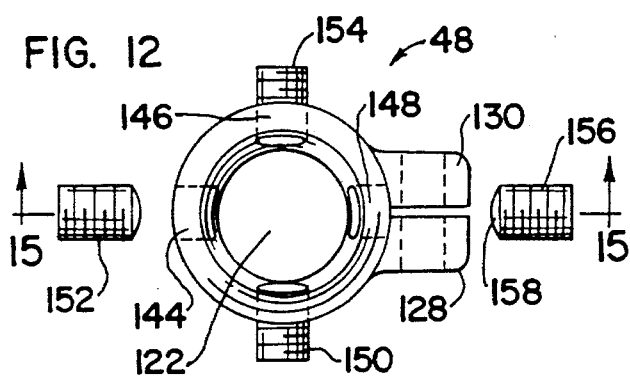
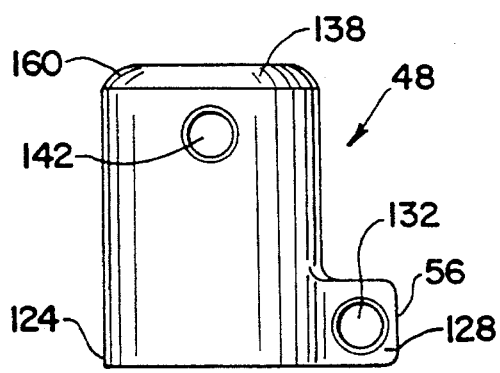
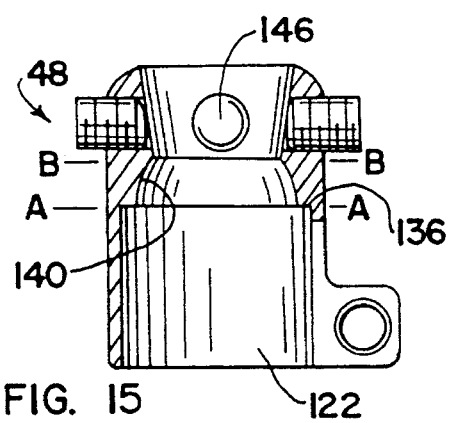
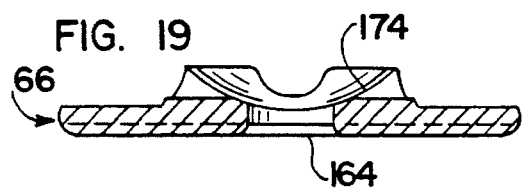
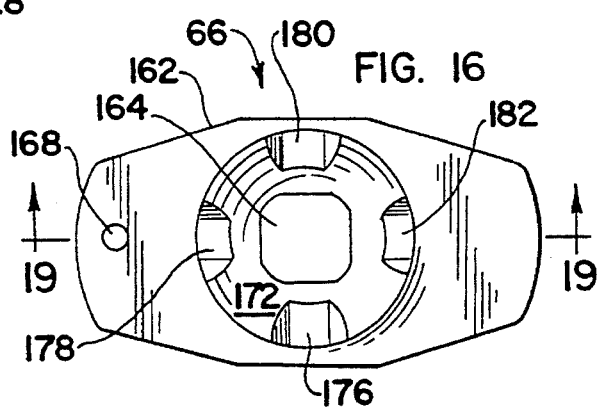
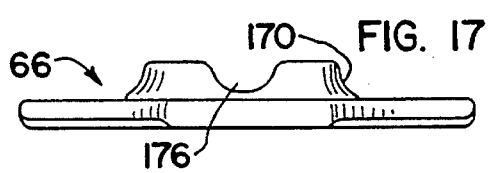
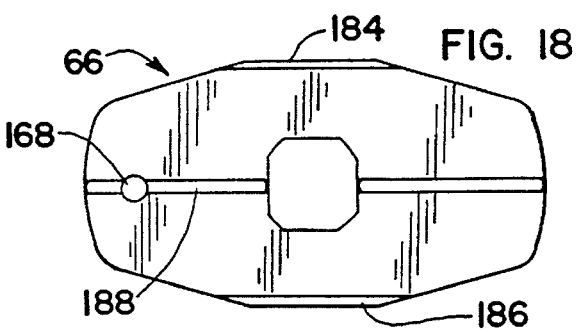

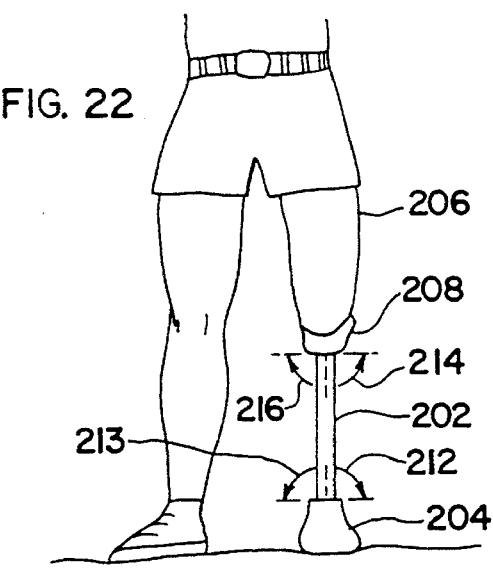
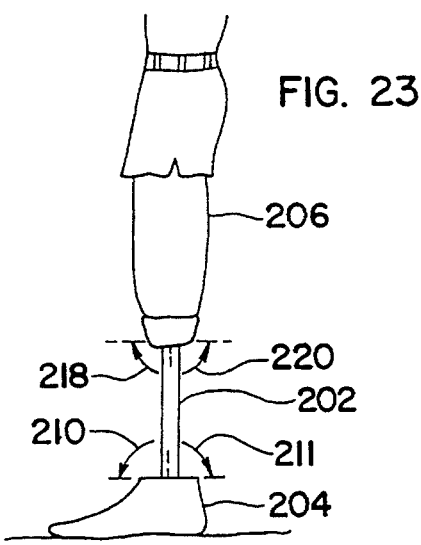
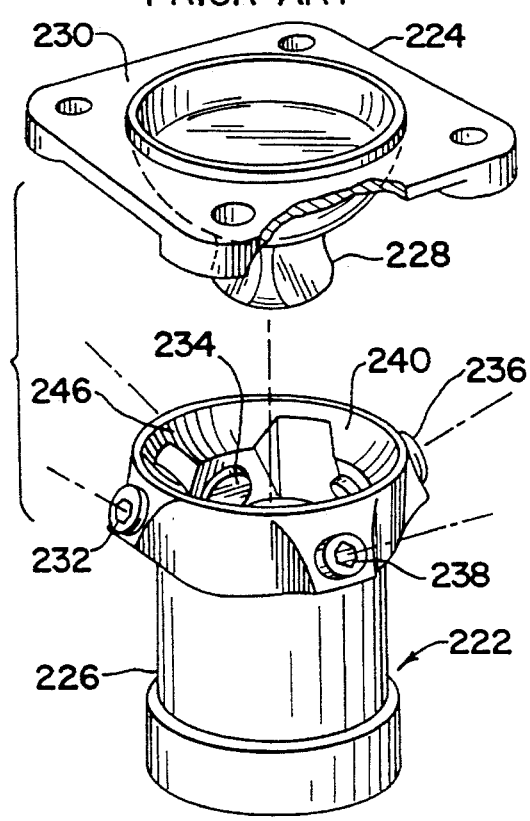
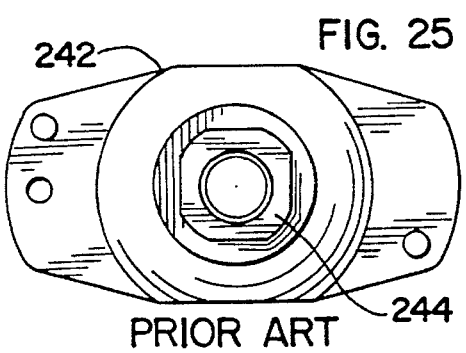
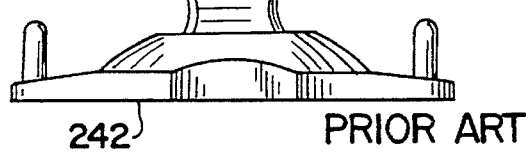
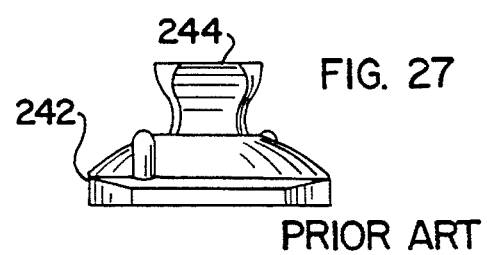

ENDOSKELETAL PROSTHESIS HAVING ADJUSTABLE COUPLING

This is a continuation of application Ser. No. 07/810,623, filed Dec. 19, 1991, now abandoned.

FIELD OF THE INVENTION

The present invention relates to the field of artificial limbs (or "prostheses"). More particularly, the invention relates to the adjustable attachment of a prosthetic device to a stump socket, artificial foot, or the like.

BACKGROUND OF THE INVENTION

A prosthesis is a device for replacing a missing part of a body, such as a leg or portion thereof. FIGS. 22 and 23 illustrate a prior art prosthetic device known as an "endoskeletal prosthesis". The endoskeletal prosthesis includes an elongated endoskeletal support member tube 202, which is typically an aluminum tube or "pylon". One end of tube 202 is connected to an artificial extremity, such as foot 204, and the other is connected to patient 206 via a stump socket 208.

The term stump refers to the end of a patient's severed limb. A stump socket is worn by a patient around the stump and a portion of the remaining limb. Typically, the stump socket is custom-made to fit a particular patient. The prosthesis is then attached to the stump socket by means of an attachment device which can be an integral part of the stump socket. Examples of such attachment devices are provided by U.S. Pat. No. 5,163,965, issued Nov. 17, 1992, the disclosure of which is hereby incorporated by reference.

When a patient is fitted for an endoskeletal prosthesis, the prosthesis must be properly aligned with the patient's stump socket and artificial foot or hand. The arrows in FIGS. 22 and 23 illustrate directions in which the endoskeletal tube 202 can be aligned with respect to stump socket 208 or foot 204. Medical practitioners generally use the following terminology to refer to these alignment adjustments: plantar and dorsi (illustrated by arrows 210 and 211, respectively, as shown in FIG. 23), inversion and eversion (illustrated by arrows 212 and 213, respectively, as shown in FIG. 22), abduction and adduction (illustrated by arrows 214 and 216, respectively, as shown in FIG. 22) and flexion and extension (illustrated by arrows 218 and 220, respectively, as shown in FIG. 23).

Attachment modules such as module 222 of FIG. 24 are commonly used to provide these alignment adjustments. Module 222 consists of an adapter plate 224 and an sleeve-like adapter 226. Adapter plate 224 is two-sided, and has a first convex side, from which a pyramid-shaped knob 228 extends. A second side 230 of adapter plate 224 is bolted to an attachment device (not shown) at the end of the stump socket. Adapter 226 itself is a hollow cylinder or sleeve. Pyramid-shaped knob 228 is inserted into one end of sleeve-like adapter 226. The other end of adapter 226 is clamped or otherwise mounted to endoskeletal pylon 202.

The plate and adaptor are then coupled using four fitment bolts or set bolts 232, 234, 236 and 238. Bolts 232–238 extend through the walls of adapter 226 and engage pyramid-shaped knob 228 to couple adapter plate 224 to adapter 226, thereby attaching endoskeletal pylon 202 to stump socket 208. By adjusting the fitment bolts, medical personnel can effect the above-described types of alignment adjustments.

When plate 224 and adapter 226 are thus coupled, they are pressed tightly together. It will be noted that top rim 240 of adapter 226 has a concave face which mates with the convex side of plate 224. Thus, no matter at what angle adapter 226 is positioned relative to plate 224, top rim 240 of adapter 226 remains in complete physical contact with the convex surface of plate 224.

Attachment module 222 shown in FIG. 24 is used to attach the upper end of an endoskeletal pylon to a stump socket. A similar arrangement is used to attach the bottom of the endoskeletal pylon to an artificial foot. When used for this purpose, a foot adapter plate 242 (shown in FIGS. 25–27) is used in lieu of stump adapter plate 224. Like adapter plate 224, foot adapter plate 242 has a pyramid-shaped knob 244 which is placed in sleeve-like adapter 226 (not shown in FIGS. 25–27).

While the foregoing prior art arrangement is workable, it has several drawbacks. Specifically, when used to attach an artificial leg, attachment module 222 is subjected to tremendous longitudinal or vertical tension and compression forces when patient 206 walks or runs which adversely affect plate 224 and adapter 226. These forces are transmitted up endoskeletal pylon 202 and to adapter 226, where they are borne by the fitment bolts, which are tightened to impinge on and hold the pyramid-shaped knob.

It will be observed that this longitudinal force is nearly perpendicular to the front faces of fitment bolts 232–238, and therefore the force is transmitted to each bolt as a shearing (as opposed to compressing) force. This shearing is resisted by the friction between the faces of fitment bolts 232–238 and pyramid-shaped knob 228. The shearing force does, however, urge bolts 232–238 to slide along and into knob 228, thereby eventually causing deformation of knob 228 and/or bolts 232–238, particularly for relatively heavy patients, such as those who weigh more than two hundred pounds. Eventually, action of the ends of bolts 232–238 against knob 228 from use of prosthetic device 200 causes significant deformation of pyramid-shaped knob 228. The result is a loosening of the coupling which can be followed by a sudden catastrophic failure of module 222. The patient's artificial leg can literally fall off in mid-stride.

To alleviate this problem, fitment bolts 232–238 in attachment module 222 extend somewhat at an angle from horizontal. This allows some component of longitudinal force to be borne as a compression force by the main body of the fitment bolts. While extending the bolts downwardly improves the performance of module 222, it also makes the fitment bolts more difficult for medical personnel to install and adjust.

Another drawback of module 222 is that reinforcements such as reinforcements 246 must be provided in the wall of sleeve-like adapter 226. These reinforcements are necessary because the fitment bolts which are lodged in the adapter wall must bear the massive longitudinal (vertical) forces discussed above. These reinforcements cause the adapter to be larger than is otherwise necessary. For a variety of reasons, particularly cosmetic, it is desirable to have a more narrow adapter.

Yet another drawback of prior art module 222 is that it uses fitment bolts or bolts having flat (as opposed to rounded) ends. These flat ends are used to improve the friction grip of the bolts. In practice, however, rounded heads provide easier alignment adjustment.

SUMMARY OF THE INVENTION

For clarity, and without limiting the scope of the invention, the terms top, bottom, front and rear are used herein to describe components as they would be oriented when used by a patient. The term "proximal" means the end of a component which is closest to a patient's head, and the term "distal" means the end of a component which is remote from the patient's head.

The present invention overcomes the above-described problems by providing an endoskeletal system having an adjustable adapter assembly which, in one embodiment, utilizes a ball joint to adjustably connect an endoskeletal pylon to a stump socket or other artificial member. The adapter assembly includes a collar adapted for attachment to the endoskeletal pylon. The interior of the collar is curved to form a first weight bearing surface. A coupling member is also provided, and is adapted for attachment to the stump socket or other artificial member. The coupling member has a curved portion which defines a second curved weight bearing surface which preferably is complementary to the first weight bearing surface.

The coupling member is placed inside the collar so that the first and second curved weight bearing surfaces engage one another to provide a selectively articulable bearing between the collar and the coupling member. Because the coupling member is connected to the stump (or other artificial member), and the collar is connected to the endoskeletal pylon, this selectively articulable bearing in effect provides an adjustable coupling between the stump socket (or other artificial member) and the endoskeletal pylon which is superior to the coupling of prior art module 222. Moreover, this selectively articulable bearing carries the large longitudinal (vertical) forces to which the adapter is subject.

In one embodiment, the adapter assembly includes a cylindrical collar. The first end of the collar is clamped around one end of an endoskeletal pylon. Near the second end, the interior bore of the collar narrows along a longitudinal portion of the collar so that the interior walls of the collar form a partial concave surface or "seat" facing toward the pylon.

In this embodiment, a ball-and-post coupler member having a curved bearing surface at one end and a (preferably) elongated attachment post at the other end. The curved bearing surface is located in the collar so that the bearing surface of the coupler member engages the seat. The curved bearing surface or the coupler is preferably sized and shaped so as to flushly fit the concave surface of the seat.

Alternatively, it is to be understood that the collar could have a convex bearing surface with the coupler having a concave bearing surface.

The attachment post extends outwardly from the second end of the collar and is bolted by a large central bolt or otherwise suitably attached to an adapter plate so that the rim of second end of the collar contacts or abuts the adapter plate, and the concave and convex spherical contours of the ball-and-post coupler and seat are securely engaged.

Near the second end of the adapter collar, four spaced-apart apertures are provided, preferably located at ninety degree intervals around the circumference of the adapter collar. In one embodiment, the apertures are threaded and fitment bolts having rounded ends are disposed in each of these apertures to engage the sides of the post disposed in the collar to secure the post in a desired position and orientation relative to the collar. These fitment bolts are used to effect various alignments between the adapter plate and the ball-and-post coupler. Unlike the prior art however, most of the massive longitudinal (vertical) forces to which the adapter assembly is subjected are borne by the curved bearing surfaces of the coupler and collar as transmitted to them by the large central bolt. The fitment bolts are relieved of most of this force, and need only absorb secondary forces, such as torsion. As a result, the fitment bolts may be horizontally oriented for easy adjustment.

BRIEF DESCRIPTION OF THE DRAWINGS

FIG. 1 is a perspective view of an endoskeletal prothesis in accordance with the invention;

FIG. 2 is an exploded perspective view of the proximal end of the endoskeletal prosthesis shown in FIG. 1;

FIG. 3 is an exploded perspective view of the distal end of the endoskeletal prosthesis shown in FIG. 1;

FIG. 4 is a bottom view of the socket adapter that forms part of the endoskeletal prosthesis shown in FIG. 2;

FIG. 5 is a top view of the socket adapter that forms part of the endoskeletal prosthesis shown in FIG. 2;

FIG. 6 is a side view of the socket adapter that forms part of the endoskeletal prosthesis shown in FIG. 2;

FIG. 7 is a sectional view of the socket adapter that forms part of the endoskeletal prosthesis shown in FIG. 5, taken along the lines 7—7;

FIG. 8 is a side view of the proximal ball-and-post coupler that forms part of the endoskeletal prosthesis shown in FIG. 2;

FIG. 9 is a top view of the proximal ball-and-post coupler that forms part of the endoskeletal prosthesis shown in FIG. 2;

FIG. 10 is a bottom view of the proximal ball-and-post coupler that forms part of the endoskeletal prosthesis shown in FIG. 2;

FIG. 11 is a sectional view of the proximal ball-and-post coupler that forms part of the endoskeletal prosthesis shown in FIG. 2, taken along the lines 11—11 in FIG. 9;

FIG. 12 is a top view of the proximal clamped collar that forms part of the endoskeletal prosthesis shown in FIG. 2;

FIG. 13 is a side view of the proximal clamped collar that forms part of the endoskeletal prosthesis shown in FIG. 2;

FIG. 14 is a rear view of the proximal clamped collar that forms part of the endoskeletal prosthesis shown in FIG. 2;

FIG. 15 is a sectional view of the proximal clamped collar that forms part of the endoskeletal prosthesis shown in FIG. 12, taken along the lines 15—15 of FIG. 12;

FIG. 16 is a top view of the foot adapter plate that forms part of the endoskeletal prosthesis shown in FIG. 2;

FIG. 17 is a side view of the foot adapter plate that forms part of the endoskeletal prosthesis shown in FIG. 2;

FIG. 18 is a bottom view of the foot adapter plate that forms part of the endoskeletal prosthesis shown in FIG. 2;

FIG. 19 is a sectional view of the foot adapter plate that forms part of the endoskeletal prosthesis shown in FIG. 16, taken along the lines 19—19 of FIG. 16;

FIG. 22 is a front view of a human patient wearing a generalized endoskeletal prosthesis;

FIG. 23 is a side view of the human patient shown in FIG. 22;

FIG. 24 is an exploded perspective view of a prior art attachment module;

FIG. 25 is a top view of a prior art foot adapter plate;

FIG. 26 is a side view of the prior art foot adapter plate shown in FIG. 25;

FIG. 27 is a front view of the foot adapter plate shown in FIG. 25;

DETAILED DESCRIPTION OF THE DRAWINGS

Figure 20:
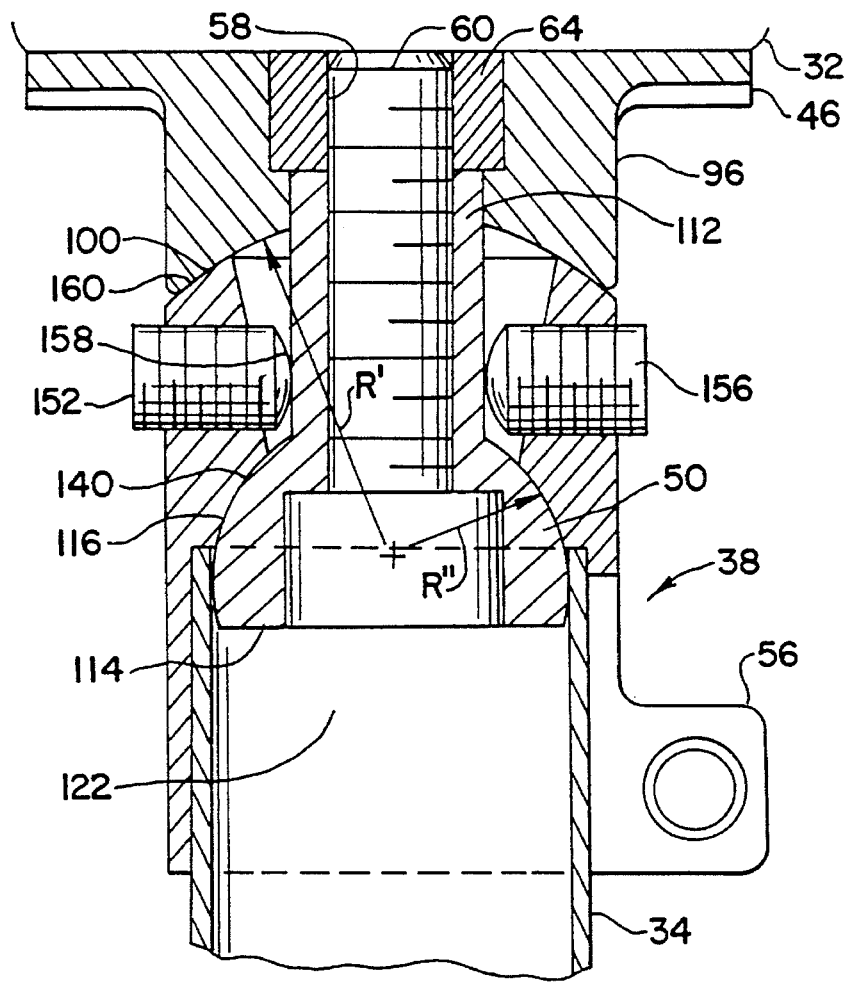
FIG. 20 is a sectional view of the proximal end of the endoskeletal system shown in FIG. 1, taken along the lines 20—20 of FIG. 1.

FIG. 1 shows a perspective view of an endoskeletal prothesis 30 which employs an embodiment of the invention. In the illustrated embodiment, endoskeletal prosthesis 30 is used to replace the lower left leg of a patient (not shown) who has undergone a below-knee amputation.

Prosthesis 30 is attached to patient's stump (not shown) by means of a stump socket 32. Prosthesis 30 generally comprises a pylon tube 34. The proximal end 36 of pylon tube 34 is connected to stump socket 32 by means of a proximal adapter assembly 38. Likewise, distal end 40 of pylon tube 34 is connected to an artificial foot 42 by means of a distal adapter assembly 44. Proximal and distal adaptor assemblies 38 and 44 are of metal, preferably stainless steel or titanium. Pylon tube 34 is preferably of aluminum or carbon graphite.

Proximal adapter assembly 38 is best illustrated in FIG. 2. Proximal adapter assembly 38 comprises a socket adapter plate 46, a proximal clamped collar 48 and a proximal ball-and-post coupler 50. Also shown in FIG. 2 is a socket coupler 52, which may be the socket coupler disclosed in U.S. Pat. No. 5,163,965 issued on Nov. 17, 1992 to James K. Rasmusson et al. and hereby incorporated by reference. Socket coupler 52 is imbedded in stump socket 32 (not shown in FIG. 2), which is in turn secured to the patient's stump. A bottom side 54 of socket coupler 52 provides a mounting surface onto which socket adapter plate 46 is bolted or otherwise suitably secured.

Proximal clamped collar 48 is secured to proximal end 36 of pylon tube 34 by means of a clamp 56 or other suitable securing device. Typically, proximal clamped collar 48 is fastened to pylon tube 34 so that clamp 56 faces rearward, and for consistency, clamp 56 is so depicted herein. Proximal ball-and-post coupler 50 has a longitudinal bore 58 for receiving a threaded proximal adapter bolt 60. Proximal adapter bolt 60 extends upwardly through bore 58 and a centrally positioned aperture 62 in socket adapter plate 46, and is received by a proximal adapter nut 64 to secure proximal ball-and-post coupler 50 to socket adapter plate 46.

It will be observed that proximal ball-and-post coupler 50 is fastened to stump socket 32 (by way of socket adapter plate 46 and socket coupler 52), and that proximal clamped collar 48 is fastened to pylon tube 34. As discussed below in detail, proximal ball-and-post coupler 50 is disposed inside proximal clamped collar 48 to form a ball type joint, thereby providing an adjustable coupling between stump socket 32 and pylon tube 34. A suitable lubricant such as a commercially available Teflon™ may be used to lubricate this joint.

Distal adapter assembly 44 is best illustrated in FIG. 3. Distal adapter assembly 44 comprises a foot adapter plate 66 (which in the illustrated embodiment is a SACH adapter plate), a distal integral collar 68 and a distal ball-and-post coupler 70. Distal ball-and-post coupler 70 is identical to proximal ball-and-post coupler 50, except that it has a threaded bore 72. Also shown in FIG. 3 is artificial foot 42 which is of nylon or wood and which is known in the art and commercially available.

Turning now to FIGS. 4–15, the structure of proximal adapter assembly 38 is now discussed in detail. FIGS. 4–7 show socket adapter plate 46. FIGS. 9–11 show proximal ball-and-post coupler 50, and FIGS. 12–15 show proximal clamped collar 48.

Referring first to FIGS. 4–7, it will be seen that socket adapter plate 46 comprises a flat and generally square-shaped base 74 having one of apertures 76 through 82 at each of its four corners. Centrally positioned aperture 62 is sized to receive proximal ball-and-post coupler 50, as discussed below in more detail. Top surface 86 of base 74 is mounted flush against bottom side 54 of socket coupler 52. Base 74 is secured to socket coupler by four bolts (not shown) which are each inserted through one of apertures 76 through 82 and received by corresponding threaded holes (not shown) in socket coupler 52. Alternatively, base 74 can be mounted to socket coupler 52 in any suitable manner.

A cylindrical stub 96 extends downwardly from and in center alignment with base 74 so that the center of stub 96 is in alignment with the center of base 74. Central aperture 62 bores through the otherwise solid cylindrical stub 96. Bottom surface 98 of stub 96 is concave along a constant radius of curvature to form a spherical contour 100 as shown in FIG. 20. Four notches 102–108 are spaced at ninety-degree angular intervals around the perimeter of bottom surface 98. These notches serve an important function which is described below in connection with FIG. 21.

As best seen in the sectional view of FIG. 7, a well 110 for receiving proximal adapter nut 64 extends through the center of base 74 and stub 96 along and around a portion of aperture 62. By placing proximal adapter nut 64 in well 110, the flat surface of base 74 can be mounted flush against the bottom side of socket coupler 52.

Referring to FIGS. 9–11, it will be seen that proximal ball-and-post coupler 50 is formed of a post 112 having a bulbous end 114. Post 112 is preferably square in lateral cross section, as best seen in the top view of FIG. 9, although post 112 may have a circular or other cross-section. Bulbous end 114 defines a curved weight bearing surface 116. Surface 116 is concave about a constant radius of curvature to form a spherical contour. Bore 58 is smooth, and runs longitudinally through post 112 and bulbous end 114. As best seen in the sectional view of FIG. 11, a well 118 for receiving head 120 of proximal adapter bolt 60 extends longitudinally along and around bore 58 through and in center alignment with a portion of bulbous end 114. Bolt 60 and ball-and-post coupler 50 can also be formed as a unitary piece.

Referring to FIGS. 12–15, it will be observed that proximal clamped collar 48 is a cylindrical body having an interior bore 122 of varying diameter. Near bottom end 124 of proximal clamped collar 48, bore 122 is sized so that collar 48 fits snugly over proximal end 36 of pylon tube 34. Proximal clamped collar 48 is then secured to pylon tube 34 by clamp 56. Clamp 56 is conventional, and comprises a longitudinal slit 126 which extends upwardly from bottom end 124 along a rearward portion of the collar's length. Clamping flanges 128 and 130 extend rearwardly from collar 48 on either side of slit 126. An aperture 132 for receiving a clamping bolt 134 (see FIG. 2) runs through clamping flanges 128 and 130 in a direction transverse to the length of slit 126. As clamping bolt 134 is tightened, clamping flanges 128 and 130 are drawn together, thereby narrowing the width of slit 126, and, effectively, decreasing the interior circumference of bore 122 along slit 126 to cause collar 48 to be tightly clamped to pylon tube 34.

As best seen in the sectional view of FIG. 15, at line A—A, the diameter of bore 122 abruptly decreases to a width less than the diameter of pylon tube 34. This abrupt change forms a ring-shaped backstop 136 which prevents pylon tube 34 from advancing toward top end 138 of proximal clamped collar 48.

Moving from line A—A toward line B—B, the diameter of bore 122 continues to narrow along a constant radius of curvature so as to form a surface or "seat" 140 having the concave contour of a portion of a sphere. The diameter of the bore 122 narrows along this contour until it reaches about 0.75 inches (at line B—B). At line B—B, the diameter of the bore begins to increase in linear relation to the distance to top end 138. As discussed below in connection with FIGS. 20 and 21, the convex spherical contour 116 of ball-and-post coupler 50 forms a weight bearing surface which engages the concave spherical contour of seat 140 to form a selectively articulable ball-type joint inside proximal clamped collar 48.

Four threaded apertures 142–148 are located at 90 degree intervals about the circumference of proximal clamped collar taken at a point about halfway between line B—B and top end 138. Apertures 142 through 148 lie on a common plane and each extends toward the central longitudinal axis of proximal clamped collar 48 and one of the four sides of post 112. Apertures 142 through 148 receive proximal adapter fitment bolts 150 through 156, respectively.

As discussed below in detail, each of proximal adapter fitment bolts 150 through 156 has a rounded end 158 which engages one of the four sides of post 112 when post 112 is disposed inside bore 122 of collar 48. Fitment bolts 150 through 156 are used to position post 112 relative to the interior of collar 48.

As the relative position of post 112 is adjusted by fitment bolts 150 through 156, so is the alignment between proximal clamped collar 48 and socket adapter plate 46. To accommodate various alignments, top end 138 of proximal clamped collar 48 is convex along a constant radius of curvature to form a partial contour 160 of a sphere. The convex contour 160 mateably engages with the concave spherical contour 100 of proximal adapter plate 46.

Turning now to FIGS. 16–19, the structure of the distal adapter assembly is now discussed in detail. Except as otherwise specified in this Specification and the Drawings, the distal adapter assembly 44 is substantially identical in construction and function to the proximal adapter assembly 38. Naturally, the orientation of the components of the distal adapter assembly 44 is inverted relative to the proximal adapter assembly 38 because the distal adapter assembly 44 is fitted to distal (i.e., opposite) end 40 of pylon tube 34.

One distinguishing characteristic of the distal adapter assembly 44 is that it includes foot adaptor plate 66 in lieu of socket adapter plate 46. As indicated, foot plate 66 is preferably a SACH plate, and is illustrated in greater detail by FIGS. 16–19. Foot adaptor plate 66 comprises a flat, elongated and octagonally-shaped base 162 which is mounted flush on top of artificial foot 42, as best seen in FIG. 1.

A centrally positioned aperture 164 in foot adapter plate 66 is sized to receive a distal adapter bolt 190, as discussed below in more detail. A single aperture 168 through base 162 receives a bolt or other suitable fastener (not shown) for securing foot plate 66 to artificial foot 42. Alternatively, base 162 can be mounted to artificial foot 42 in any suitable manner.

A cylindrical stub 170 extends upwardly from and in center alignment with base 162. Central aperture 164 bores through the otherwise solid cylindrical stub 170. The bottom surface 172 of stub 170 is concave along a constant radius of curvature to form a spherical contour 174. Four notches 176–182 are spaced at ninety-degree angular intervals around the perimeter of bottom surface 172. These notches serve an important function which will become apparent latter.

As best seen in FIG. 18, the underside of base 162 has parallel longitudinal ridges 184, 186 and 188 along the base's medial side, lateral side and longitudinal center line, respectively. Ridges 184, 186 and 188 are conventional, and are used for the purpose of gripping against the top surface of foot 42 to prevent relative movement between base 162 and foot 42 during torsional loads.

Distal integral collar 68 is identical to proximal clamped collar 48, except that distal integral collar 68 is glued and pinned (as opposed to clamped) to distal (as opposed to proximal) end 40 of pylon tube 34. Persons skilled in the art will readily observe that there are numerous ways to attach distal integral collar 68 to pylon tube 34, and the present invention contemplates all such methods.

In a preferred embodiment, distal integral collar 68 is sized to fit over distal end 40 of pylon tube 34 leaving a 0.005 inch bond line for adhesive bonding. Preferably, an epoxy should be used which is suitable for bonding dissimilar types of metal (in this case, aluminum and stainless steel). One such epoxy is the Versalock™ acrylic structural adhesive made by Lord Corporation of Erie, Pa. A roll pin (not shown) should also be diametrically inserted through distal integral collar 68 and pylon tube 34 where the collar superimposes the tube.

Distal ball-and-post coupler 70 is identical to proximal ball-and-post coupler 50, except that bore 72 through distal ball-and-post coupler 70 is threaded to receive distal adapter bolt 190. As best seen in FIG. 3, artificial foot 42 includes an aperture 192 suitable for receiving threaded distal adapter bolt 190. Distal adapter bolt 190 is inserted upwardly through a washer 194, aperture 192 (of artificial foot 42), and central aperture 164 (of foot plate 66), and is received by threaded bore 72 of distal ball-and-post coupler 70 to secure distal ball-and-post coupler 70 to artificial foot 42.

It will be observed that distal ball-and-post coupler 70 is fastened to artificial foot 42, and that distal integral collar 68 is fastened to pylon tube 34. As discussed below in connection with the operation of proximal adapter assembly 38, distal ball-and-post coupler 70 is disposed inside distal integral collar 68 to form a selectively articulable ball type joint, thereby providing a adjustable coupling between pylon tube 34 and artificial foot 42.

The remaining elements of distal adapter assembly 44 are substantially identical in structure and function to their counterparts in proximal adapter assembly 38, and a separate discussion thereof will not be undertaken.

Figure 21:
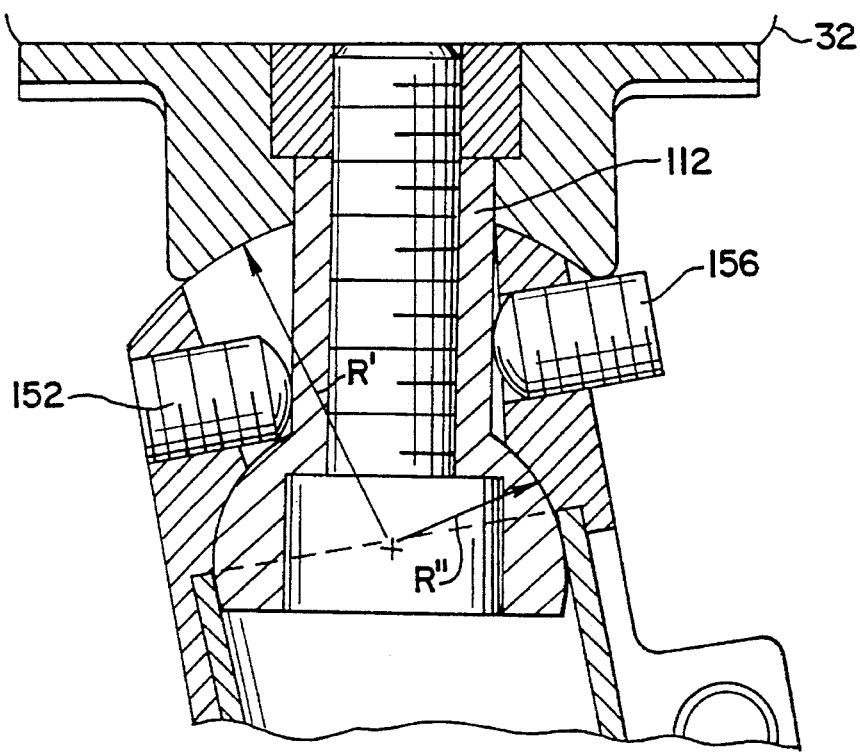
FIG. 21 is the same sectional view of the proximal end of the endoskeletal system shown in FIG. 20, showing the use of fitment bolts to adjust the alignment of the proximal adapter plate relative to the proximal pylon adapter assembly.

Referring to FIGS. 20 and 21, the structural and functional aspects of the present invention are most clearly illustrated. FIG. 20 is a sectional view of proximal clamped adapter assembly 38. Proximal ball-and-post coupler 50 is disposed inside bore 122 of proximal clamped collar 48 so that the convex spherical contour 116 of bulbous end 114 mateably engages with the concave spherical contour of seat 140 formed by the interior walls of bore 122. The interface of surfaces 116 and 140 form a selectively articulable bearing which is particularly suitable for withstanding the large longitudinal tension forces discussed above. It will be observed that these surfaces 116 and 140 must be machined to conform to the contour of identical spheres having radius R" of 0.5 inches. Preferably, the tolerance of the radius of convex surface 116 of bulbous end 114 is +0, −0.003 inches, and the tolerance of the concave radius of seat 140 is +0.003, −0 inches.

Proximal adapter bolt 60 extends upwardly through bore 58 of proximal ball-and-post coupler 50 and is received by proximal adapter nut 64 to tightly secure proximal ball-and-post coupler 50 to socket adaptor plate 46. As proximal adapter bolt 60 is tightened, it urges convex contour 116 of bulbous end 114 into tight mateable engagement with concave seat 140. This, in turn, urges convex spherical contour 160 of the top of proximal clamped collar 48 into a second tight mating engagement with concave spherical contour 100 of bottom surface 98 of socket adaptor plate 46. The interface of surfaces 100 and 160 form an articulable bearing which is particularly suited for withstanding longitudinal compression forces which are exerted as proximal adapter assembly 38 by the weight of the patient.

It will be observed that this second set of mating surfaces 100 and 160 must be machined to conform to the contour of identical spheres having radius R' of 1.030 inches. Preferably, the tolerance of the radius of convex surface 160 of collar 48 is +0, −0.002 inches, and the tolerance of the radius of concave surface 100 of adapter plate 46 is +0.002, −0 inches.

As indicated, proximal clamped collar 48 is secured to proximal end 36 of pylon tube 34 by clamp 56, while proximal ball-and-post coupler 50 is secured to stump socket 32 via socket adapter plate 46. The engagement of convex spherical surface 116 and concave seat 140 create an articulable bearing between ball-and-post coupler 50 and proximal clamped collar 48, thereby providing an adjustable coupling between stump socket 32 and pylon tube 34.

The relative position of proximal clamped collar 48 to ball-and-post coupler 50 is fixed by the four fitment bolts 150–156. Two of these fitment bolts, posterior bolt 152 and anterior bolt 156, are shown in FIGS. 20 and 21. For the purposes of illustration, ball-and-post coupler 50 is in a parallel alignment with clamped collar 48. Consequently, pylon tube 34 extends straight down from stump socket 32. Fitment bolts 152 and 156 are each inserted an equal distance through apertures 144 and 148, respectively, and impinge on opposing sides of post 112 so that pylon tube 34 has no angle of flexion or extension relative to stump socket 32.

The mating of spherical contour 116 and 140, and 100 and 160 provide a sliding interface which enables the relative positions of socket adapter plate 46 and proximal clamped collar 48 to be selectively adjusted, such as shown in FIG. 21. This adjustment is effected by tightening one of proximal adapter fitment bolts 150–156 by a particular amount, and loosening by that same amount the diametrically opposing fitment bolt.

For example, in FIG. 21, anterior fitment bolt 152 has been tightened one turn, and posterior fitment bolt 156 has been loosened by one turn, thus forcing post 112 of ball-and-post coupler 50 toward the posterior side of bore 122, thereby sliding proximal clamped collar 48 along bearing surfaces 100, 116, 140 and 160 into a different alignment with socket adapter plate 46 to provide a flexion angle or adjustment to pylon tube 34 (as shown in FIG. 21). This process can be reversed, or can be repeated with lateral and medial fitment bolts 150 and 154 to provide a full range of abduction/adduction and flexion/extension alignments.

It will be observed that in larger angles of adjustment, such as shown in FIG. 21, fitment bolts, such as bolt 156, will impinge on adapter plate 46 (or, in the case of distal adapter assembly 44, foot plate 66). To prevent this impingement, notches 102–108 on adapter plate 46 are positioned over fitment bolts 150–156, respectively. These notches provide clearance for the ends of the fitment bolts when clamped collar 48 is adjusted at an angle such as shown in FIG. 21.

The distal adapter assembly operates in the same fashion to provide a full range of plantar/dorsi and inversion/eversion adjustments between pylon tube 34 and artificial foot 42.

While the invention has been described with respect to certain preferred embodiments, variations, modifications, substitutions and alternatives will be apparent to those skilled in the art of prosthetics, and accordingly the scope of the invention is defined by the appended claims. Specifically, it is understood that the invention may be practiced with arm and leg prosthetic devices. Additionally, fitment bolts 150–156 may be substituted by other known techniques for adjustably holding ball-and-post coupler 50 in fixed angular relation to a collar such as clamped collar 48. Collars 48 and 68 may be fastened to pylon tube 34 (or other suitable endoskeletal system) by any suitable manner, and need not be clamped or glued, as illustrated. While bearing surfaces such as contours 100, 116, 140 and 160 are preferably spherical, said surfaces need not be curved around a constant radius of curvature or form a continuous surface.

I claim:

1. A prosthesis device for adjustably coupling an endoskeletal member having a longitudinal axis to an object comprising:

an elongated cylindrical collar having a first open end, a second end adapted for engagement with the endoskeletal member; a longitudinal bore between said first and second ends, wherein said bore narrows along a portion of the collar to form a first curved weight bearing surface, and an upper rim on said first open end which defines a second curved weight bearing surface;

a plurality of fitment apertures spaced at intervals about a perimeter portion of and extending through said collar, said apertures extending in a direction normal to the longitudinal axis of said collar;

an elongated post having one end which flares outwardly to define a ball that is semi-spherical and complementary in shape to said first curved weight bearing surface, wherein said post is longitudinally disposed within said collar so that said ball engages said first curved surface engaged to provide a first articulable load bearing coupling;

a plurality of fitment bolts, each inserted into a different one of said fitment apertures to engage said post for holding said post in fixed angular relation to said collar; and a plate having a first side adapted for rigid attachment to the object and a second side having means for securing said post to said plate; wherein said second side defines a weight bearing surface that is complementary to said second weight bearing surface, wherein said second side engages said second weight bearing surface to provide a second articulable load bearing coupling;

wherein said plate further comprises a well for receiving the end of said post which is remote from said ball member, wherein said post and the interior of said well have mating rectilinear contours.

2. The prosthesis of claim 1 wherein said post includes a longitudinal bore for receiving a bolt, said plate includes a threaded aperture for receiving said bolt, and said securing means further comprises a bolt inserted through said post portion's longitudinal bore and said plate aperture.

3. The apparatus of claim 1 wherein said post has a plurality of substantially flat side portions, and whereby each of said plurality of fitment bolts engages one of said flat side portions.

4. The apparatus of claim 1 wherein said collar is a single-piece tubular member.

5. The apparatus of claim 4 wherein said fitment apertures are located between said first and second curved weight bearing surfaces.

6. The prosthesis device according to claim 1 wherein each of said plurality of fitment bolts is substantially horizontal.

7. The prosthesis device according to claim 1 wherein the bore of said collar at said second end is slightly larger than the width of the endoskeletal member so that said second end is positionable over an end of the endoskeletal member.

8. The prosthesis device according to claim 7 wherein the bore of said collar narrows sharply at a point between said first curved surface and said second end to form a backstop for preventing the endoskeletal member from extending through said collar beyond said backstop.

9. The prosthesis device for attachment to a stump socket comprising:
   an endoskeletal pylon;
   an elongated cylindrical collar having a distal and a proximal end, a plurality of fitment apertures spaced at intervals about a perimeter portion of and extending through said collar, and having a contoured longitudinal bore defining a first semispherical weight bearing surface that is concave facing toward said distal end, wherein said proximal end defines a second semispherical weight bearing surface, and said apertures extend in a direction normal to the longitudinal axis of said collar;
   a ball-and-post member having an elongated post with a semispherical end that defines a convex weight bearing surface which is wider than said post, wherein said ball-and-post member is longitudinally disposed in said collar so that said semispherical end engages said first weight bearing surface to provide a first articulable coupling between said ball-and-post and said collar, and said post extends toward said proximal end of said collar, said post having at least two flat elongated sides;
   a plate having a proximal side adapted for rigid attachment to the stump socket and having a distal side which defines a curved weight bearing surface;
   first securing means for securing said ball-and-post member to said plate so that said distal side of said plate engages said second semispherical surface to provide a second articulable coupling;
   a plurality of fitment bolts oriented substantially normal to the longitudinal axis of the endoskeletal pylon, each of said fitment bolts being inserted through one of said fitment apertures to engage a different one of said post's elongated flat sides.

10. The prosthesis device of claim 9 wherein said distal side of said plate further comprises a downwardly extending portion on which said curved weight bearing surface is formed; wherein said downwardly extending portion has a plurality of peripheral notches spaced at angular intervals to provide clearance for said fitment bolts.

11. The apparatus of claim 9 wherein said post has a plurality of substantially flat side portions, and whereby each of said plurality of fitment bolts engages one of said flat side portions.

12. The apparatus of claim 9 wherein said collar is a single-piece tubular member.

13. The apparatus of claim 9 wherein said fitment apertures are located between said first and second semispherical weight bearing surfaces.

14. The prosthesis device according to claim 9 wherein each of said plurality of fitment bolts is substantially horizontal.

15. The prosthesis device according to claim 9 wherein the bore of said collar at said distal end is slightly larger than the width of the endoskeletal pylon so that said distal end is positionable over an end of the endoskeletal pylon.

16. The prosthesis device according to claim 15 wherein the bore of said collar narrows sharply at a point between said first curved surface and said distal end to form a backstop for preventing the endoskeletal pylon from extending through said collar beyond said backstop.

17. The prosthesis device according to claim 9 wherein said plate further comprises a well for receiving the end of said post which is remote from said ball, wherein said post and the interior of said well have mating rectilinear contours.

18. The prosthesis according to claim 9 wherein said post includes a longitudinal bore for receiving a bolt, said plate includes a threaded aperture for receiving said bolt, and said securing means further comprises a bolt inserted through said post portion's longitudinal bore and said plate aperture.

19. A prosthesis device for adjustably coupling an endoskeletal member having a longitudinal axis to an object comprising:
   an elongated cylindrical collar having a first open end, a second end adapted for engagement with the endoskeletal member; a longitudinal bore between said first and second ends, wherein said bore narrows along a portion of the collar to form a first curved weight bearing surface, and an upper rim on said first open end which defines a second curved weight bearing surface;
   a plurality of fitment apertures spaced at intervals about a perimeter portion of and extending through said collar, said apertures extending in a direction normal to the longitudinal axis of said collar;
   an elongated post having one end which flares outwardly to define a ball that is semi-spherical and complementary in shape to said first curved weight bearing surface, wherein said post is longitudinally disposed within said collar so that said ball engages said first curved surface engaged to provide a first articulable load bearing coupling;
   a plurality of fitment bolts, each inserted into a different one of said fitment apertures to engage said post for holding said post in fixed angular relation to said collar; and
   a plate having a first side adapted for rigid attachment to the object and a second side having means for securing said post to said plate; wherein said second side defines a weight bearing surface that is complementary to said second weight bearing surface, wherein said second side engages said second weight bearing surfaces to provide a second articulable load bearing coupling; wherein said post includes a longitudinal bore for receiving a bolt, said plate includes a threaded aperture for receiving said bolt, and said securing means further comprises a bolt inserted through said post portion's longitudinal bore and said plate aperture.

20. The apparatus of claim 19 wherein said post has a plurality of substantially flat side portions, and whereby each of said plurality of fitment bolts engages one of said flat side portions.

21. The apparatus of claim 19 wherein said collar is a single-piece tubular member.

22. The apparatus of claim 19 wherein said fitment apertures are located between said first and second curved weight bearing surfaces.

23. The prosthesis device according to claim 19 wherein each of said plurality of fitment bolts is substantially horizontal.

24. The prosthesis device according to claim 19 wherein the bore of said collar at said second end is slightly larger than the width of the endoskeletal member so that said second end is positionable over an end of the endoskeletal member.

25. The prosthesis device according to claim 24 wherein the bore of said collar narrows sharply at a point between said first curved surface and said second end to form a backstop for preventing the endoskeletal member from extending through said collar beyond said backstop.

26. The prosthesis device according to claim 19 wherein said plate further comprises a well for receiving the end of said post which is remote from said ball, wherein said post and the interior of said well have mating rectilinear contours.

27. A prosthesis device for adjustably coupling an endoskeletal member having a longitudinal axis to an object, comprising:

a tubular collar having a first open end, a second end adapted for engagement with the endoskeletal member, a plurality of fitment apertures spaced at intervals about a perimeter portion of and extending through said collar, said apertures extending in a direction normal to the longitudinal axis of said collar; and a longitudinal bore between said first and second ends, wherein the bore of said collar narrows along a longitudinal portion of the collar to form a first curved weight-bearing surface, wherein said perimeter portion is located between said first curved weight-bearing surface and said first end;

a ball-and-post member which includes an elongated post having elongated sides and terminating in a semispherical end that defines a second curved weight-bearing surface complementary to said first curved weight-bearing surface, said post having a rectilinear transverse cross-section, and having a width that is less than said semispherical end wherein said ball-and-post member is disposed in said collar so that said first and second curved surfaces engage to provide a load-bearing coupling;

a plurality of substantially horizontal fitment bolts, each inserted into a different one of said fitment apertures to engage the elongated sides of said post for holding said post in a fixed angular relation to said collar; and a plate having a first side adapted for rigid attachment to the object and a second side adapted for attachment to said post;

wherein the bore of said collar at said second end is slightly larger than the width of the endoskeletal member so that said second end is positionable over an end of the endoskeletal member; and further that the bore of said collar narrows sharply at a point between said first curved surface and said second end to form a backstop for preventing the endoskeletal member from extending through said collar beyond said backstop; and wherein said first open end of said collar has an upper rim which defines a third curved weight-bearing surface, and wherein said second side of said plate defines a fourth weight-bearing surface which is complementary to said third weight-bearing surface, wherein said third and fourth weight-bearing surfaces engage to form an articulable compression-bearing interface when said ball-and-post member is disposed in said collar to form said coupling and said plate is secured to said post.

* * * * *